United States Patent
Ritchie et al.

(10) Patent No.: US 8,211,902 B2
(45) Date of Patent: *Jul. 3, 2012

(54) QUINAZOLINONE DERIVATIVES USEFUL AS VANILLOID ANTAGONISTS

(75) Inventors: Timothy John Ritchie, Horsham (GB); Andrew James Culshaw, Horsham (GB); Christopher Thomas Brain, Horsham (GB); Edward Karol Dziadulewicz, Horsham (GB); Terance William Hart, High Peak (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/089,943

(22) Filed: Apr. 19, 2011

(65) Prior Publication Data

US 2011/0195983 A1 Aug. 11, 2011

Related U.S. Application Data

(63) Continuation of application No. 11/569,802, filed as application No. PCT/EP2005/006253 on Jun. 8, 2005, now Pat. No. 7,960,399.

(30) Foreign Application Priority Data

Jun. 8, 2004 (GB) .................................. 0412769.2

(51) Int. Cl.
*A61K 31/517* (2006.01)
(52) U.S. Cl. ..................................... 514/266.3; 544/290
(58) Field of Classification Search ............... 514/266.3; 544/290
See application file for complete search history.

(56) References Cited

U.S. PATENT DOCUMENTS

| | | | |
|---|---|---|---|
| 2,749,344 A | 6/1956 | Hitchings et al. |
| 3,317,388 A | 5/1967 | Shetty et al. |
| 3,793,326 A | 2/1974 | Muren |
| 3,864,362 A | 2/1975 | Feuer et al. |
| 4,501,755 A | 2/1985 | Wu |
| 4,841,076 A | 6/1989 | Kitagawa et al. |
| 4,841,077 A | 6/1989 | Ito et al. |
| 5,284,853 A | 2/1994 | Levin et al. |
| 5,294,617 A | 3/1994 | Venkatesan et al. |
| 5,830,909 A | 11/1998 | Crandall |
| 5,948,775 A | 9/1999 | Koko et al. |
| 5,958,930 A | 9/1999 | Gangjee |
| 6,335,180 B1 | 1/2002 | Julius et al. |
| 6,476,076 B1 | 11/2002 | Lee et al. |
| 6,500,853 B1 | 12/2002 | Seehra et al. |
| 6,723,730 B2 | 4/2004 | Bakthavatchalam et al. |
| 6,790,629 B2 | 9/2004 | Julius et al. |
| 7,097,991 B2 | 8/2006 | Julius et al. |
| 2003/0049728 A1 | 3/2003 | Julius et al. |
| 2003/0158198 A1 | 8/2003 | Lee et al. |
| 2003/0220227 A1 | 11/2003 | Gungor et al. |
| 2004/0138454 A1 | 7/2004 | Culshaw et al. |
| 2005/0095650 A1 | 5/2005 | Julius et al. |
| 2005/0182045 A1 | 8/2005 | Nagase et al. |
| 2006/0154942 A1 | 7/2006 | Culshaw et al. |
| 2008/0114056 A1 | 5/2008 | Ritchie et al. |
| 2008/0194595 A1 | 8/2008 | Ritchie et al. |
| 2008/0293939 A1 | 11/2008 | Culshaw et al. |
| 2009/0082365 A1 | 3/2009 | Bhalay et al. |
| 2010/0144740 A1 | 6/2010 | Fox et al. |
| 2010/0197705 A1 | 8/2010 | Chen et al. |

FOREIGN PATENT DOCUMENTS

| | | |
|---|---|---|
| DE | 239090 | 11/1906 |
| DE | 1 232 152 | 1/1967 |
| EP | 1 047 711 B1 | 8/2003 |
| EP | 1 009 804 B1 | 10/2003 |
| EP | 1 398 032 A1 | 3/2004 |
| EP | 1 600 440 A1 | 11/2005 |
| FR | 1367738 A | 6/1964 |
| FR | 1412615 A | 10/1965 |
| FR | 2 167 642 | 8/1973 |
| GB | 936902 | 9/1963 |
| GB | 1003802 | 9/1965 |
| GB | 1076747 A | 7/1967 |
| GB | 1 495 305 | 12/1977 |
| JP | 62-193605 A | 8/1987 |
| JP | 7-258224 A | 10/1995 |
| JP | 10-259176 A | 1/1998 |
| SU | 1 262 927 A1 | 11/1997 |
| WO | WO 92/13535 A1 | 8/1992 |

(Continued)

OTHER PUBLICATIONS

Chen, U.S. PTO Restriction Requirement, U.S. Appl. No. 12/683,317, Nov. 3, 2011, 9 pgs.

(Continued)

*Primary Examiner* — James O Wilson
*Assistant Examiner* — Douglas M Willis
(74) *Attorney, Agent, or Firm* — Paul D. Strain, Esq.; Strain & Strain PLLC

(57) ABSTRACT

The present invention relates to the use of a quinazolinone compound of the formula (I) wherein $R_1$, $R_2$, $R_3$, $R_4$, $R_5$ and m are as defined in the specification and in the claims, in free form or in salt form, and, where possible, in acid addition salt form, as a vanilloid.

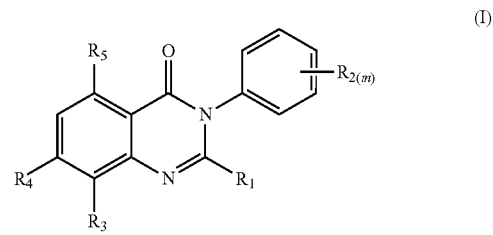

(I)

7 Claims, No Drawings

FOREIGN PATENT DOCUMENTS

| | | |
|---|---|---|
| WO | WO 95/03293 A1 | 2/1995 |
| WO | WO 95/18616 A2 | 7/1995 |
| WO | WO 97/28118 A1 | 8/1997 |
| WO | WO 97/44041 A1 | 11/1997 |
| WO | WO 98/02162 A1 | 1/1998 |
| WO | WO 98/11438 A1 | 3/1998 |
| WO | WO 98/18781 A2 | 5/1998 |
| WO | WO 98/29403 A1 | 7/1998 |
| WO | WO 99/09140 A1 | 2/1999 |
| WO | WO 99/43654 A2 | 9/1999 |
| WO | WO 01/17985 A1 | 3/2001 |
| WO | WO 01/70228 A1 | 9/2001 |
| WO | WO 02/08221 A2 | 1/2002 |
| WO | WO 02/28851 A1 | 4/2002 |
| WO | WO 02/076946 A2 | 10/2002 |
| WO | WO 02/083143 A1 | 10/2002 |
| WO | WO 03/014064 A1 | 2/2003 |
| WO | WO 03/048132 A1 | 6/2003 |
| WO | WO 03/106435 A1 | 12/2003 |
| WO | WO 2004/005265 A1 | 1/2004 |
| WO | WO 2004/033435 A1 | 4/2004 |
| WO | WO 2004/041755 A2 | 5/2004 |
| WO | WO 2004/072051 A1 | 8/2004 |
| WO | WO 2005/023782 A1 | 3/2005 |
| WO | WO 2005/040112 A1 | 5/2005 |
| WO | WO 2005/049613 A1 | 6/2005 |
| WO | WO 2005/120510 A1 | 12/2005 |
| WO | WO 2005/121116 A1 | 12/2005 |
| WO | WO 2006/122200 A1 | 11/2006 |
| WO | WO 2010/084050 A2 | 7/2010 |

OTHER PUBLICATIONS

"Diazonium-Verbindungen", Roempp Chemie Lexikon, Version 1.0, Thieme Verlag 1995 (E 8).

Al-Maharik et al., "Synthesis of C-C-Bridged Bis-Isoflavones", Journal of Organic Chemistry, vol. 65, No. 8 (2000), pp. 2305-2308.

Anirudhan et al., "The Chemistry of the "Insoluble Red" Woods. Part X. Syntheses of Isoflavans, Isoflav-3-enes, and Isoflavylium salts", J. Chem. Soc. (C) (1966), pp. 629-633.

Bae et al., "Synthesis of pyrido[2,3-d]pyrimidines via palladium-catalyzed reaction of iodouracil with acetylenes", Tetrahedron Letters, vol. 41, No. 31 (2000), pp. 5899-5902.

Bhalay, U.S. PTO Office Action, U.S. Appl. No. 12/095,995, Mar. 29, 2010, 11 pgs.

Bhalay, U.S. PTO Restriction Requirement, U.S. Appl. No. 12/095,995, Sep. 28, 2009, 9 pgs.

Bhalay; U.S. PTO Office Action, U.S. Appl. No. 12/095,995, Nov. 29, 2010, 10 pgs.

Bogert et al., "Researches on Quinazolines (Twenty-Seventh Paper). The Synthesis of 3-Aminoaryl-4-Quinazolones from Acylanthranils and Aromatic Diamines", Contribution from the Havemeyer Laboratories of Columbia University No. 190 (1911), XP-002453809, pp. 949-962.

Bogert et al., "Researches on Quinazolines (Twenty-Third Paper). On 6-Methyl-7-Aminoquinazolones, 7-Nitroquinazolone-6-Carboxylic Acids, and 1,3,7,9-Naphthotetrazines", Contribution from the Havemeyer Laboratories of Columbia University No. 169 (1909), XP-002453810, pp. 1071-1078.

Bondarenko et al., "Synthesis of 3',4'-Dimethoxyisoflavone Derivatives", Chemistry of Natural Compounds, vol. 39, No. 4 (2003), pp. 340-343.

Bondarenko et al., "Synthesis of Formononetin Analogs", Chemistry of Natural Compounds, vol. 39, No. 4 (2003), pp. 344-348.

Brady et al., "Intramolecular [2 + 2] Ketene Cycloadditions. Synthesis of Isoflavones and 3-Aroylbenzofurans", Journal of Organic Chemistry, vol. 53, No. 7 (1988), pp. 1353-1356.

Breuer et al., "Beziehungen zwischen chemischer Konstitution und pharmakologischer Wirkung bei aminosubstituierten 3-Aryl-4(3H)-chinazolinonen", Arzneimittel-Forschung, vol. 21, No. 2 (1971) pp. 238-243 + Abstract.

Chemical Abstracts, "3-Phenylquinazolones", Olin Mathieson Chemical Corp., vol. 62 (1965), 1672a-e, 1 pg.

Culshaw, U.S. PTO Notice of Allowance, U.S. Appl. No. 10/469,756, May 28, 2010, 6 pgs.

Culshaw, U.S. PTO Office Action, U.S. Appl. No. 10/469,756, Jun. 2, 2006, 11 pgs.

Culshaw, U.S. PTO Office Action, U.S. Appl. No. 10/469,756, Sep. 7, 2007, 9 pgs.

Culshaw, U.S. PTO Office Action, U.S. Appl. No. 10/469,756, Dec. 14, 2009, 16 pgs.

Culshaw, U.S. PTO Office Action, U.S. Appl. No. 10/530,897, Jun. 4, 2007, 14 pgs.

Culshaw, U.S. PTO Restriction Requirement, U.S. Appl. No. 10/469,756, Sep. 4, 2009, 5 pgs.

Daenens et al., "Biotransformation of Mecloqualone in Man", Arzneimittel-Forschung, vol. 24, No. 2 (1974), pp. 195-202 + Abstract.

Dave et al., "Pyridopyrimidines: Part III-Synthesis and Analgesic Activity of 4-Aminopyrido [2,3-d] pyrimidines", Indian Journal of Pharmaceutical Sciences, vol. 48, No. 3 (1986), pp. 75-77.

Dörwald, "Side Reactions in Organic Synthesis: A Guide to Successful Synthesis Desgin", Weinheim: WILEY-VCH Verlag GmbH & Co. KGaA, (2005), Preface.

Edwards et al., "Antineoplastic activity and cytotoxicity of flavones, isoflavones, and flavanones", Journal of Natural Products, vol. 42, No. 1 (1979), pp. 85-91.

El-Sharief et al., "A Comparative Study of the Behavior of Cyanothioformamide and Oxazolidine (Thiones or Iminothiones) Towards Some Binucleophiles", Heteroatom Chemistry, vol. 13, No. 4 (2002), pp. 291-298.

English translation of Japanese Office Action dated May 18, 2010, 2 pgs.

Ericsonn et al., "Methaqualone metabolites", Acta Pharmaceutica Suecica, vol. 10, No. 4 (1973), pp. 257-262 + Abstract.

Fox et al., "Highly Active and Selective Catalysts for the Formation of $\alpha$-Aryl Ketones", J. Am. Chem. Soc., vol. 122 (2000), pp. 1360-1370.

Fukui et al., Chemical Abstract No. 1963:448229, "Synthesis of 7-hydroxy-2', 4', 5'-trimethoxyisoflavone and related compounds", Chemical Abstracts, vol. 59, No. 8 (1963), 2 pgs.

Goodman and Gilman's, "The Pharmacological Basis of Therapeutics", 7th edition, Macmillan Publishing, p. 1807 and p. 1827 (1985) (BM 4).

Grindsteins et al., "Synthesis of new derivatives of pyrido[2,3-d]pyrimidines", Hcaplus 77:88424, Accession No. 1972:488424 HCAPLUS (1972), 1 pg.

J. March, "Advanced Organic Chemistry", 4th edition, Wiley, p. 1216, 1992 (E 6).

Jordan, V.C. Nature Reviews: Drug Discovery, vol. 2 (2003), pp. 205-213.

Joshi et al,, "Studies in Quinazolones: Part I—Synthesis & Spectral Characteristics of Substituted 2-Isopropyl-4(3H)-quinazolones", Indian Journal of Chemistry, vol. 16B (1978), pp. 1067-1072.

Kacker et al., "Potential Analgesics. Part I. Synthesis of Substituted 4-Quinazolones", Journal of the Indian Chemical Society, vol. 28 (1951), pp. 344-346.

Korte et al., "Synthese purinähnlicher Heterocyclen", Chem Ber, vol. 85 (1952), pp. 1012-1019.

Kukla et al., "Insecticidal Properties & Chemical Constitution: Part VII-Allylated Isoflavone Derivatives",Database Accession No. 1964:3073, Indian Journal of Chemistry, vol. 1 (1963), pp. 343-345.

Kurosawa et al., Chemical Abstract No. 91:20255, "Reactions of 2'—hydroxyisoflavone and 2' -hydroxy-2-methylisoflavones with metal salts", Chemical Abstracts, vol. 91 (1979), p. 631.

Levai et al., "A comparative study of the epoxidation of 2-substituted isoflavones by dimethyldioxirane, sodium hypochlorite, and alkaline hydrogen peroxide (Weitz-Scheffer reaction)", Journal of Heterocyclic Chemistry, vol. 37, No. 5 (2000), pp. 1065-1069.

Levine et al., "TRP channels: Targets for the relief of pain", Biochimica et Biophysica Acta, vol. 1772 (2007), pp. 989-1003.

Liu et al and Hauxue 1966, 19(6), 582-586, Chemical Abstract No. 132:78525, "Study on synthesis and catalytic mechanism of coenzyme model of methionine synthase", Chemical Abstracts, vol. 132, No. 7, (2000), p. 666.

Martin et al., "A Convenient Alternative Route to β-Aminoketones", Tetrahedron, vol. 50, No. 7 (1994), pp. 2255-2264.
Matyus et al., "Some Aspects of the Chemistry of Pyrido[2,3-d]pyrimidines. A Novel s-Triazolo[4',3':1,6]pyrido[2,3-d]pyrimidine", Liebigs Ann Chem, vol. 10 (1984), pp. 1653-1661.
McIntyre et al., "Pharmacological differences between the human and rat vanilloid receptor 1 (VR1)", British Journal of Pharmacology, vol. 132 (2001), pp. 1084-1094.
Merck Safety Data Sheet:, Acetic Acid (Last Revision Feb. 22, 2002) (E 7).
Moersch et al., "Antifertility activity of isoflavones related to genistein", Journal of Medicinal Chemistry, vol. 10, No. 2 (1967), pp. 154-158.
Oguchi et al., Chemical Abstract No. 133:261086, "Molecular Design, Synthesis, and Hypoglycemic Activity of a Series of Thiazolidine-2,4-diones", J. Med. Chem., vol. 43, No. 16 (2000), pp. 3052-3066.
Parikh et al., "Some Pharmacological Studies on 2-Methyl-3-(3,5-dimethyl-4-hydroxyphenyl)-3,4-dihydroquinazolin-4-one (SRC-226) and its Derivatives", The Indian Journal of Pharmacy, vol. 38, No. 3 (1976), pp. 89-90.
Parmar et al., "Fragmentation pathways in the mass spectra of 2-methylisoflavone derivatives. Useful in their diagnosis", Journal of the Indian Chemical Society, vol. 64, No. 1 (1987), pp. 64-66.
PCT Search Report, International Application No. PCT/EP02/03332, Sep. 23, 2002, 8 pgs.
Pedersen, "Phosphorammides: III. Phenyl N,N-Dimethylphosphorodiamidate as a New Reagent for the Synthesis of 3-Methyl-4-oxo-3,4-dihydroquinazolines", Communications Synthesis (1977), XP-002453982, pp. 180-181.
Petrow et al., "Some 5-Azaquinoxalines and 4-Azabenziminazoles", J Chem Soc (1948), pp. 1389-1392.
Ritchie, U.S. PTO Notice of Allowance, U.S. Appl. No. 11/569,802, Jan. 11, 2010, 13 pgs.
Ritchie, U.S. PTO Notice of Allowance, U.S. Appl. No. 11/569,802, Feb. 2, 2010, 5 pgs.
Ritchie, U.S. PTO Notice of Allowance, U.S. Appl. No. 11/569,802, Oct. 26, 2010, 13 pgs.
Ritchie, U.S. PTO Notice of Allowance, U.S. Appl. No. 11/569,802, Jan. 31, 2011, 13 pgs.
Ritchie, U.S. PTO Office Action, U.S. Appl. No. 11/569,802, Mar. 4, 2009, 18 pgs.
Ritchie, U.S. PTO Office Action, U.S. Appl. No. 11/569,802, Sep. 4, 2009, 13 pgs.
Ritchie, U.S. PTO Restriction Requirement, U.S. Appl. No. 11/569,802, Oct. 15, 2008, 9 pgs.
Ritchie, U.S. PTO Office Action, U.S. Appl. No. 11/570,049, Jan. 12, 2010, 6 pgs.
Ritchie, U.S. PTO Office Action, U.S. Appl. No. 11/570,049, May 7, 2009, 13 pgs.
Ritchie, U.S. PTO Office Action, U.S. Appl. No. 11/570,049, May 27, 2010, 5 pgs.
Ritchie, U.S. PTO Restriction Requirement, U.S. Appl. No. 11/570,049, Aug. 11, 2008, 7 pgs.
Ritchie, U.S. PTO Supplemental Notice of Allowability, U.S. Appl. No. 11/569,802, Nov. 9, 2010, 7 pgs.
Ritchie, U.S. PTO Supplemental Notice of Allowability, U.S. Appl. No. 11/569,802, Feb. 9, 2011, 10 pgs.
Ritchie, U.S. PTO Supplemental Notice of Allowability, U.S. Appl. No. 11/569,802, Feb. 15, 2011, 6 pgs.
Robins et al., "Studies on Condensed Pyrimidine Systems. XII. Synthesis of Some 4- and 2,4-Substituted Pyrido[2,3-d]pyrimidines", J Am Chem Soc, vol. 77 (1955), pp. 2256-2260.
Robins et al., "Studies on Condensed Pyrimidine Systems. XIX. A New Synthesis of Pyrido[2,3-d]pyrimidines. The Condensation of 1,3-Diketones and 3-Ketoaldehydes with 4-Aminopyrimidines", J Am Chem Soc, vol. 80, No. 13 (1958), pp. 3449-3457.
Roh et al., "Palladium-Catalyzed Coupling Reaction of Iodouracil Having Acetamidine Moiety With Olefins", Synthetic Communications, vol. 30, No. 1 (2000), pp. 81-86.
Shao et al., Chemical Abstract No. 94:174809, "Studies on the synthesis and structure-antihypoxia activity relations of daidzein, an active principle of Pueraria pseudohiruta, and its derivatives", Chemical Abstracts, vol. 94 (1981), p. 701.
Shetty et al., "6-Aminoquinazolinones as Potent Analgetic Agents", CNS (Cent. Nerv. Syst.) Drugs, Symp. (1966), pp. 156-169, Publisher: Council of Scientific & Industrial Research, New Delhi, India.
Sinha et al., "Quinazolones: Part XI—Effect of Substituents on Claisen Rearrangement of Allyloxyquinazolones", Indian Journal of Chemistry, vol. 24B (1985), pp. 1182-1184.
Somasekhara et al., "3-Aryl-2-isoPropyl and 2-Aryl-3-isoPropyl Derivatives of 4-(3H)-Quinazolinones", The Indian Journal of Pharmacy, vol. 33, No. 1 (1971), pp. 26-27.
Somasekhara et al., "Some new derivatives of 3,4-dihydroquinazolin-4-one of pharmacological interest", The Indian Journal of Pharmacy, vol. 27, No. 1 (1965), pp. 12-13 + Abstract.
The Merck Index, 11th edition, Merck & Co, p. 1848 (1989) (BM 5).
The Merck Index, 11th edition, Merck & Co, p. 2107 (1989) (BM 6).
Trattner et al., "Deamination Studies on Pyrimidine and Condensed Pyrimidine Systems", J Org Chem, vol. 29 (1964), pp. 2674-2677.
Troschuetz et al., "Versuche zur Synthese von pharmakologisch wirksamen Heterocyclen via Mannich-Reaction, 3. Mitt. Pyrido[2,3-d]pyrimidin-2,4-dione (5-Desazapteridine)", Arch. Pharm. (Weinheim), vol. 311, No. 5 (1978), pp. 406-414.
Tschitschibabin et al., "α,β'-Diamino-pyridin and α,β-Diamino-pyridin", Chem Ber, vol. 60 (1927), pp. 766-776.
Vilain, Chemical Abstract No. 91-69937, "Ichthyocidal properties of rotenoids and isoflavones", Chemical Abstracts, vol. 91 (1979), p. 186.
Wall et al., "A Multisubstrate Adduct Inhibitor of AICAR Transformylase", Journal of Medicinal Chemistry, vol. 42, No. 18 (1999), pp. 3421-3424.
William Martindale, "Extra Pharmacopoeia", 25th edition, The Pharmaceutical Press, pp. 1453-1467, 1967 (BM 1).
William Martindale, "The Extra Pharmacopoeia", 31st edition, Royal Pharmaceutical Society, pp. 686-687 (1996) (BM 7).
William Martindale, "The Extra Pharmacopoeia", 31st edition, Royal Pharmaceutical Society, p. xi (1996) (BM 3).
William Martindale, "The Extra Pharmacopoeia", 31st edition, Royal Pharmaceutical Society, p. 1511 (1996) (BM 2).
Wolff, Burgers Medicinal Chemistry and Drug Discovery—Fifth Edition, New York: John Wiley & Sons, (1996), vol. 1, pp. 975-977.
Yutilov et al., Chemical Abstract No. 128:257435, "Preparation of 6-bromo-5-methylimidazo[4,5-b]-pyridine", Chemical Abstracts, vol. 128, No. 21 (1998), p. 585.
Bhalay, U.S. PTO Notice of Allowance, U.S. Appl. No. 12/095,995, Apr. 28, 2011, 8 pgs.
Culshaw, U.S. PTO Office Action, U.S. Appl. No. 11/950,079, Apr. 28, 2011, 15 pgs.
Szallasi et al., "Vanilloid (Capsaicin) Receptors and Mechanisms", Pharmacological Reviews, The American Society for Pharmacology and Experimental Therapeutics, vol. 51, No. 2 (1999), pp. 159-211.
Ritchie, U.S. PTO Restriction Requirement, U.S. Appl. No. 13/434,248, Apr. 26, 2012, 9 pgs.
Chen, U.S. PTO Office Action, U.S. Appl. No. 12/683,317, Feb. 24, 2012, 52 pgs.

QUINAZOLINONE DERIVATIVES USEFUL AS VANILLOID ANTAGONISTS

CROSS-REFERENCE TO RELATED PATENT APPLICATIONS

This application is a Continuation of U.S. application Ser. No. 11/569,802, filed Jan. 4, 2007, now U.S. Pat. No. 7,960,399 which is the National Stage of International Application No. PCT/EP2005/006253, filed Jun. 8, 2005, which is based upon and claims the benefit of priority from prior United Kingdom Patent Application No. 0412769.2, filed Jun. 8, 2004, the entire contents of all of which are incorporated herein by reference in their entirety.

SUMMARY

The present invention relates to the use of quinazolinone derivatives as vanilloid antagonists, to certain novel quinazolinone derivatives, to processes for preparing them, to their use as pharmaceuticals and to pharmaceutical compositions containing them.

DETAILED DESCRIPTION

In a first aspect, the present invention relates to the use of a quinazolinone compound of the formula

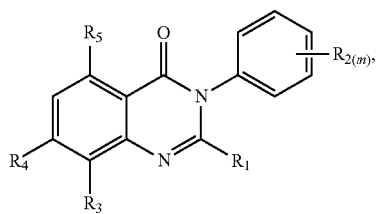

(I)

wherein
$R_1$ is $C_1$-$C_6$alkyl, $(C_1$-$C_6$alkyl$)C_1$-$C_6$alkyl, di-$(C_1$-$C_6$alkyl)$C_1$-$C_6$alkyl, $C_3$-$C_6$cycloalkyl, $(C_1$-$C_6$alkyl)amino or di-$(C_1$-$C_6$alkyl)amino;

each $R_2$, independently, is halogen, $C_1$-$C_6$alkyl, halogen-substituted $C_1$-$C_6$alkyl, hydroxy$C_1$-$C_6$alkyl, cyano or a group —C(=O)—$R_{2a}$, where $R_{2a}$ is $C_1$-$C_6$alkyl;

$R_3$ is hydrogen, halogen, $C_1$-$C_6$alkyl, $C_2$-$C_6$alkenyl, $C_2$-$C_6$alkynyl, hydroxy, hydroxy-substituted $C_1$-$C_6$alkyl, $C_1$-$C_6$alkoxy, $C_3$-$C_6$cycloalkyl, cyano, —C(=O)H, phenyl, $(C_3$-$C_6$cycloalkyl$)C_1$-$C_6$alkoxy, $(C_1$-$C_6$alkoxycarbonylamino$)C_1$-$C_6$alkoxy or $(C_1$-$C_6$alkylcarbonylamino$)C_1$-$C_6$alkoxy;

$R_4$ is hydroxy, esterified hydroxy, etherified hydroxy, amino, $(C_1$-$C_6$alkyl)amino, a group

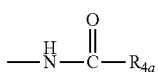

or a group

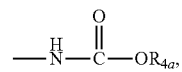

where $R_{4a}$ is $C_1$-$C_6$alkyl or halogen-substituted $C_1$-$C_6$alkyl, or a group

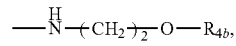

where $R_{4b}$ is benzyl or phenylethyl;
$R_5$ is hydrogen or hydroxy; and
m is 1 or 2,
in free form or in salt form, and, where possible, in acid addition salt form, as a vanilloid antagonist.

In a special embodiment of the first aspect, the present invention relates to the use of a quinazolinone compound of the formula I, wherein $R_1$ is $C_1$-$C_6$alkyl, $(C_1$-$C_6$alkyl$)C_1$-$C_6$alkyl, di-$(C_1$-$C_6$alkyl)$C_1$-$C_6$alkyl or $C_3$-$C_6$cycloalkyl;

each $R_2$, independently, is halo, $C_1$-$C_6$alkyl, tri-halo substituted $C_1$-$C_6$alkyl, hydroxy$C_1$-$C_6$alkyl or a group

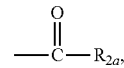

where $R_{2a}$ is $C_1$-$C_6$alkyl;
$R_3$ is hydrogen, halo, $C_1$-$C_6$alkyl, hydroxy, $C_1$-$C_6$alkoxy or $(C_3$-$C_6$cycloalkyl$)C_1$-$C_6$alkoxy;
$R_4$ is hydroxy, esterified hydroxy, etherified hydroxy, amino, $(C_1$-$C_6$alkyl)amino, a group

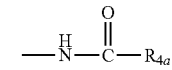

or a group

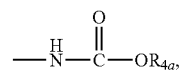

where $R_{4a}$ is $C_1$-$C_6$alkyl, or a group

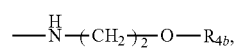

where $R_{4b}$ is benzyl or phenylethyl;
$R_5$ is hydrogen or hydroxy; and
m is 1 or 2,
in free or salt form and, where possible, in acid addition salt form, as a vanilloid antagonist.

In a second aspect, the present invention relates to novel quinazolinone compounds of the formula

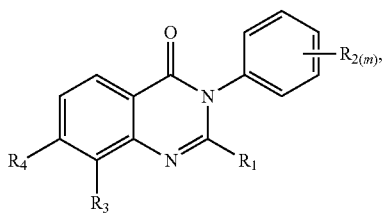 (Ia)

wherein
R$_1$ is C$_1$-C$_6$alkyl, (C$_1$-C$_6$alkyl)C$_1$-C$_6$alkyl, di-(C$_1$-C$_6$alkyl)C$_1$-C$_6$alkyl, C$_3$-C$_6$cycloalkyl, (C$_1$-C$_6$alkyl)amino or di-(C$_1$-C$_6$alkyl)amino;

each R$_2$, independently, is halogen, C$_1$-C$_6$alkyl, halogen-substituted C$_1$-C$_6$alkyl, hydroxyC$_1$-C$_6$alkyl, cyano or a group —C(=O)—R$_{2a}$, where R$_{2a}$ is C$_1$-C$_6$alkyl;

R$_3$ is hydrogen, halogen, C$_1$-C$_6$alkyl, C$_2$-C$_6$alkenyl, C$_2$-C$_6$alkynyl, hydroxy, hydroxy-substituted C$_1$-C$_6$alkyl, C$_1$-C$_6$alkoxy, C$_3$-C$_6$cycloalkyl, cyano, —C(=O)H, phenyl, (C$_3$-C$_6$cycloalkyl)C$_1$-C$_6$alkoxy, (C$_1$-C$_6$alkoxycarbonylamino)C$_1$-C$_6$alkoxy or (C$_1$-C$_6$alkylcarbonylamino)C$_1$-C$_6$alkoxy;

R$_4$ is hydroxy, esterified hydroxy, etherified hydroxy, amino, (C$_1$-C$_6$alkyl)amino, a group

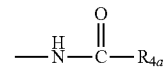

or a group

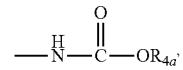

where R$_{4a}$ is C$_1$-C$_6$alkyl or halogen-substituted C$_1$-C$_6$alkyl, or a group

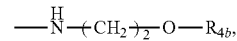

where R$_{4b}$ is benzyl or phenylethyl; and
m is 1 or 2,
in free form or in salt form, and, where possible, in acid addition salt form.

In a special embodiment of the second aspect, the present invention relates to novel quinazolinone compounds of the formula Ia, wherein
R$_1$ is C$_1$-C$_6$alkyl, (C$_1$-C$_6$alkyl)C$_1$-C$_6$alkyl, di-(C$_1$-C$_6$alkyl)C$_1$-C$_6$alkyl or C$_3$-C$_6$cycloalkyl;

each R$_2$, independently, is halo, C$_1$-C$_6$alkyl, tri-halo substituted C$_1$-C$_6$alkyl, hydroxyC$_1$-C$_6$alkyl or a group

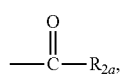

where R$_{2a}$ is C$_1$-C$_6$alkyl;
R$_3$ is hydrogen, halo, C$_1$-C$_6$alkyl, hydroxy, C$_1$-C$_6$alkoxy or (C$_3$-C$_6$cycloalkyl)C$_1$-C$_6$alkoxy;

R$_4$ is hydroxy, esterified hydroxy, etherified hydroxy, amino, (C$_1$-C$_6$alkyl)amino, a group

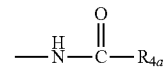

or a group

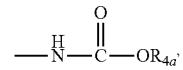

where R$_{4a}$ is C$_1$-C$_6$alkyl, or a group

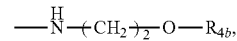

where R$_{4b}$ is benzyl or phenylethyl; and
m is 1 or 2,
in free or salt form and, where possible, in acid addition salt form.

Terms used in this specification have the following meanings:

"C$_1$-C$_6$alkyl" denotes straight-chain or branched C$_1$ to C$_6$-alkyl, e.g., methyl ethyl, n-propyl, isopropyl, n-butyl, isobutyl, sec-butyl or tert-butyl.

"C$_1$-C$_6$alkoxy" denotes straight-chain or branched C$_1$ to C$_6$-alkyl-oxy, e.g., methoxy, ethoxy, n-propoxy or isopropoxy.

"Halo" denotes halogen which may be I, Br, Cl or F.

"Esterified hydroxy" denotes acyloxy, preferably C$_1$-C$_6$alkanoyloxy, more preferably C$_1$-C$_4$alkanoyloxy.

"Etherified hydroxy" denotes C$_1$-C$_6$alkoxy, preferably C$_1$-C$_4$alkoxy.

The quinazolinone compounds of the invention exist in free or salt form and, where possible, in acid addition salt form. The invention is to be understood as including the compounds of formulae (I) and (Ia) in free or salt form and, where possible, in acid addition salt form. In the latter connection, suitable pharmaceutically acceptable acid addition salts for pharmaceutical use in accordance with the invention include, in particular, the hydrochloride salt.

In formulae (I) and (Ia), the following significances are preferred independently, collectively or in any combination or sub-combination:

(a) R$_1$ is C$_1$-C$_4$alkyl, (C$_1$-C$_4$alkyl)C$_1$-C$_4$alkyl, di-(C$_1$-C$_4$alkyl)C$_1$-C$_4$alkyl or cyclopropyl;

(b) each R$_2$, independently, is chloro, fluoro, C$_1$-C$_4$alkyl, trifluoro-substituted C$_1$-C$_4$alkyl, more preferably trifluoromethyl, C$_1$-C$_4$alkylcarbonyl, more preferably methylcarbonyl, or hydroxyC$_1$-C$_4$alkyl, more preferably hydroxymethyl;

(c) R$_3$ is hydrogen, chloro, bromo, C$_1$-C$_4$alkyl, hydroxy, C$_1$-C$_4$alkoxy or (C$_3$-C$_8$cycloalkyl)C$_1$-C$_4$alkoxy; and (d) R$_4$ is hydroxy, amino, (C$_1$-C$_4$alkyl)amino or a group

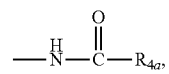

where R$_{4a}$ is C$_1$-C$_4$alkyl.

In a third aspect, the present invention relates to processes for preparing the compounds of formula (Ia) as depicted in the following reaction schemes:

A. For preparing compounds of formula (Ia), where $R_1$ and $R_2$ are as defined above, $R_3$ is as defined for a compound of formula I, $R_4$ is amino and m is 1.

B. For preparing compounds of formula (Ia), where $R_1$ and $R_2$ are as defined above, $R_3$ is as defined for a compound of formula I, $R_4$ is hydroxy and m is 1.

Scheme A

First step:

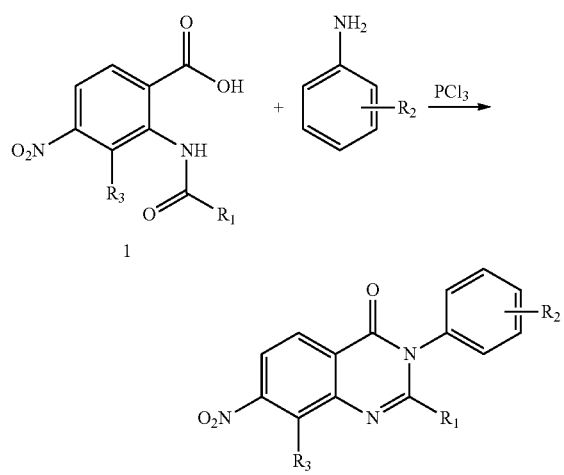

General Description:

The first step of Scheme A involves the condensation/cyclisation of the amide compound of formula 1 with a substituted aniline compound in the presence of phosphorus trichloride to obtain the 7-nitro substituted quinazolin-4-one compound of formula 2.

Second Step:

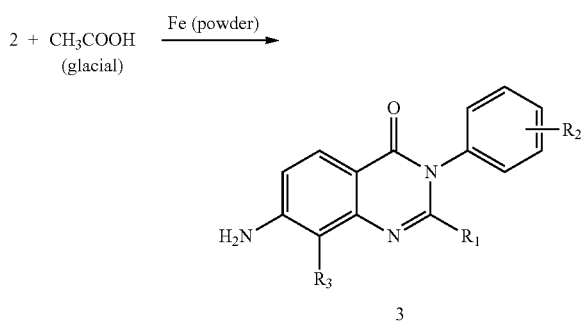

General Description:

The second step of Scheme A involves the reduction of the 7-nitro substituted quinazolin-4-one compound of formula 2 with glacial acetic acid and iron powder to obtain the 7-amino substituted quinazolin-4-one compound of formula 3.

The corresponding alkylamines, amides and carbamates may be prepared by methods described in the literature utilising a compound of formula 3. More particularly, the alkylamines may be prepared by subjecting a compound of formula 3 to reductive alkylation utilising an appropriate aldehyde or ketone. Alternatively, a compound of formula 3 may be reacted with a $C_1$-$C_6$alkyl halide. The amides may be prepared by acylating a compound of formula 3 with an appropriate acyl chloride. The carbamates may be prepared by reacting a compound of formula 3 with an appropriate alkylchloroformate.

Scheme B

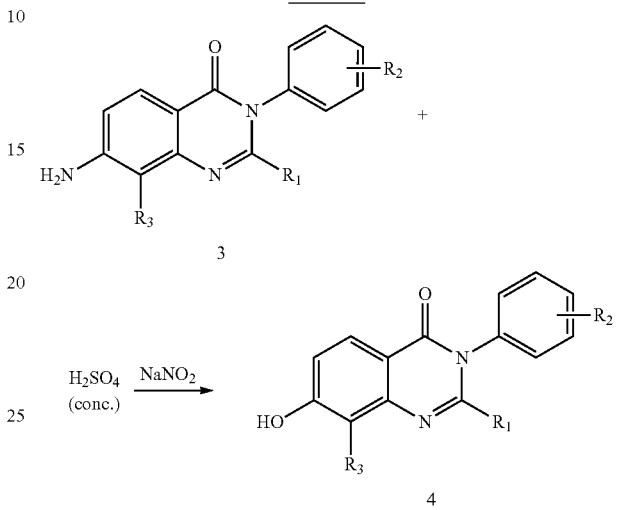

General Description:

Scheme B involves the Sandmeyer reaction of the 7-amino substituted quinazolin-4-one compound of formula 3 which was prepared as set forth in Scheme A, with concentrated sulphuric acid and sodium nitrite to obtain the 7-hydroxy substituted quinazolin-4-one compound of formula 4.

The starting compounds in Scheme A are known compounds which are commercially available.

Working up the reaction mixtures according to the above processes and purification of the compounds thus obtained may be carried out in accordance with known procedures.

Acid addition salts may be produced from the free bases in known manner, and vice-versa.

Compounds of formulae (I) and (Ia) in optically pure form can be obtained from the corresponding racemates according to well-known procedures, e.g., HPLC with chiral matrix. Alternatively, optically pure starting materials can be used.

Stereoisomeric mixtures, e.g., mixtures of diastereomers, can be separated into their corresponding isomers in a manner known per se by means of suitable separation methods. Diastereomeric mixtures, e.g., may be separated into their individual diastereomers by means of fractionated crystallisation, chromatography, solvent distribution and similar procedures. This separation may take place either at the level of a starting compound or in a compound of formula (I) or (Ia) itself. Enantiomers may be separated through the formation of diastereomeric salts, e.g., by salt formation with an enantiomer-pure chiral acid, or by means of chromatography, e.g., by HPLC, using chromatographic substrates with chiral ligands.

In any additional process steps, carried out as desired, functional groups of the starting compounds which should not take part in the reaction may be present in unprotected form or may be protected, e.g., by one or more of the protecting groups mentioned below. The protecting groups are then wholly- or partly-removed according to one of the methods described there.

The protecting groups may already be present in precursors and should protect the functional groups concerned against unwanted secondary reactions. It is a characteristic of protecting groups that they lend themselves readily, i.e., without undesired secondary reactions, to removal, typically by solvolysis, reduction, photolysis or also by enzyme activity, e.g., under conditions analogous to physiological conditions, and that they are not present in the end-products. The skilled artisan knows, or can easily establish, which protecting groups are suitable with the reactions mentioned hereinabove and hereinafter.

The protection of such functional groups by protecting groups, the protecting groups themselves, and their removal reactions are described, e.g., in standard reference works, such as J. F. W. McOmie, *Protective Groups in Organic Chemistry*, Plenum Press, London and NY (1973); T. W. Greene, *Protective Groups in Organic Synthesis*, Wiley, NY (1981); *The Peptides*; Volume 3, E. Gross and J. Meienhofer, Eds., Academic Press, London and NY (1981); *Methoden der organischen Chemie (Methods of organic chemistry)*, Houben Weyl, 4$^{th}$ Edition, Volume 15/1, Georg Thieme Verlag, Stuttgart (1974); H. D. Jakubke and H. Jescheit, *Aminosauren, Peptide, Proteine (Amino acids, peptides, proteins)*, Verlag Chemie, Weinheim, Deerfield Beach, and Basel (1982); and Jochen Lehmann, *Chemie der Kohlenhydrate: Monosaccharide und Derivate (Chemistry of carbohydrates: monosaccharides and derivatives)*, Georg Thieme Verlag., Stuttgart (1974).

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, e.g., ion exchangers, typically cation exchangers, e.g., in the H$^+$ form, depending on the type of reaction and/or reactants at reduced, normal or elevated temperature, e.g., in the range from −100° C. to about 190° C., preferably from about −80° C. to about 150° C., e.g., at −80° C. to 60° C., at room temperature, at −20° C. to 40° C. or at the boiling point of the solvent used, under atmospheric pressure or in a closed vessel, where appropriate under pressure, and/or in an inert atmosphere, e.g., under argon or nitrogen.

Preferred compounds of formula (I) are those wherein
$R_1$ is $C_1$-$C_4$alkyl, ($C_1$-$C_4$alkyl)$C_1$-$C_4$alkyl or $C_3$-$C_6$cycloalkyl;
$R_2$ is chloro, fluoro, $C_1$-$C_4$alkyl, trifluoro-substituted $C_1$-$C_4$alkyl, $C_1$-$C_4$alkylcarbonyl or hydroxy$C_1$-$C_4$alkyl;
$R_3$ is hydrogen, chloro, bromo, hydroxy, $C_1$-$C_4$alkyl, hydroxy, $C_1$-$C_4$alkoxy or ($C_3$-$C_6$cycloalkyl)$C_1$-$C_4$alkoxy;
$R_4$ is hydroxy, amino or ($C_1$-$C_4$alkyl)amino;
$R_5$ is hydrogen or hydroxy; and
m is 1 or 2.

More preferred compounds of formula (I) are those wherein
$R_1$ is $C_1$-$C_4$alkyl, ($C_1$-$C_4$alkyl)$C_1$-$C_4$alkyl or $C_3$-$C_6$cycloalkyl;
$R_2$ is chloro, fluoro, $C_1$-$C_4$alkyl, trifluoromethyl, methylcarbonyl or hydroxymethyl;
$R_3$ is hydrogen, chloro, bromo, $C_1$-$C_4$alkyl, hydroxy or $C_1$-$C_4$alkoxy;
$R_4$ is hydroxy, amino or ($C_1$-$C_4$alkyl)amino;
$R_5$ is hydrogen or hydroxy; and
m is 1.

Preferred compounds of formula (Ia) are those wherein
$R_1$ is $C_1$-$C_4$alkyl, ($C_1$-$C_4$alkyl)$C_1$-$C_4$alkyl or $C_3$-$C_6$cycloalkyl;
$R_2$ is chloro, fluoro, $C_1$-$C_4$alkyl, trifluoro-substituted $C_1$-$C_4$alkyl, $C_1$-$C_4$alkylcarbonyl or hydroxy$C_1$-$C_4$alkyl;
$R_3$ is hydrogen, chloro, bromo, $C_1$-$C_4$alkyl, hydroxy, $C_1$-$C_4$alkoxy or ($C_3$-$C_6$cycloalkyl)$C_1$-$C_4$alkoxy;
$R_4$ is hydroxy, amino or ($C_1$-$C_4$alkyl)amino; and
m is 1 or 2.

More preferred compounds of formula (Ia) are those wherein
$R_1$ is $C_1$-$C_4$alkyl, ($C_1$-$C_4$alkyl)$C_1$-$C_4$alkyl or $C_3$-$C_6$cycloalkyl;
$R_2$ is chloro, fluoro, $C_1$-$C_4$alkyl, trifluoromethyl, methylcarbonyl or hydroxymethyl;
$R_3$ is hydrogen, chloro, bromo, $C_1$-$C_4$alkyl, hydroxy, $C_1$-$C_4$alkoxy or ($C_3$-$C_6$cycloalkyl)$C_1$-$C_4$alkoxy;
$R_4$ is hydroxy, amino or ($C_1$-$C_4$alkyl)amino; and
m is 1.

The even more preferred compounds of the formula I or Ia are the compounds of the Examples 1 to 29, especially of the Examples 1 to 28.

Another aspect of this invention relates to the fact that the compounds of formulae (I) and (Ia) and their pharmaceutically acceptable salts and, where possible, pharmaceutically acceptable acid addition salts, have beneficial pharmacological activity and, therefore, are useful as pharmaceuticals. In particular, the compounds of formulae (I) and (Ia) exhibit human vanilloid antagonistic activity. More particularly, the compounds of formulae (I) and (Ia) are active at the TRPVI receptor as demonstrated by their ability to inhibit capsaicin and low pH activation of the TRPVI ion channel as follows:

Chinese Hamster Ovary-K1 (CHO-K1) cells, transfected to express either the human, rat or guinea pig TRPV1 receptor, were grown in Minimal Essential Media (MEM) alpha medium without nucleosides supplemented with fetal calf serum (10%), 2 mM L-glutamine, 100 IU/mL penicillin, 100 μg/mL streptomycin and 350-700 μg/mL geneticin. All reagents were supplied by Invitrogen. Cells were grown in T-175 flasks or Costar black, clear-bottomed 96-well view plates and maintained at 37° C. in a 90% humidified incubator with an atmosphere of 5% $CO_2$ and 95% air. The cells were passaged twice a week at a ratio of 1:10 to 1:20 to maintain steady growth. For experimentation, cells were harvested at approximately 80% confluency and plated onto view plates at 40,000 cells per well in 100 μL media and grown overnight.

Calcium Mobilisation Assay

On the day of the capsaicin assay, media was aspirated and cells were washed with 100 μL 10 mM N-2-(hydroxyethylpiperazine-N'-[2-ethane-sulfonic acid] (HEPES) buffered Hank's Balanced Salt Solution (HBSS), pH 7.4. Cells were then incubated for 40 minutes with 2.3 μM of the ratiometric calcium binding dye fura-2/AM (from Molecular Probes), made up in HEPES buffered HBSS, containing 0.01% pluronic F-127. For the pH assay, HEPES was omitted and the pH of HBSS adjusted to 7.4. After washing twice with 100 μL assay buffer, cells were incubated for 10 minutes with 100 μL of test compounds (made up in HBSS, pH 7.4), in duplicate, at concentrations between 0.001 and 30 μM. The plate was then placed in a Molecular Devices Flexstation. The TRPV1 receptor was stimulated by application of either capsaicin or low pH. For testing the effect of compounds for possible antagonism, capsaicin was used at the EC$_{80}$ concentration which was 0.05 μM for the rat TRPV1 receptor, and 0.1 μM for the human and guinea pig. For pH experiments, a low pH buffered solution [60 mM 2-[N-morpholino]ethane sulfonic acid (MES) in HBSS] was added to the assay wells to give a final pH of 5.5.

For determinations of antagonist IC$_{50}$ values (concentrations of antagonist that inhibit responses to either pH 5.5 or capsacin by 50%), at least 10 antagonist concentrations were measured in duplicate. The response in the presence of the antagonist was calculated as a percentage of the control response to capsaicin or low pH and was plotted against the concentration of antagonist. The $IC_{50}$ was estimated by non-linear regression analysis to sigmoidal-logistic curves by Activity-Base software (v5.0.10) or Microcal Origin (v7.03). These values were averaged (means and standard error of the mean) for at least three independent experiments.

The compounds of formulae (I) and (Ia), e.g., the compounds of Examples 1-28, show TRPVI receptor antagonist activity having $IC_{50}$ values in the range 0.004-30 μM.

In view of the above, the compounds of formulae (I) and (Ia) are useful as vanilloid receptor blockers, e.g., in the treatment of diseases and conditions in which vanilloid receptor activation plays a role or is implicated. Such conditions include, in particular, pain, e.g., bone and joint pain (osteoarthritis), cancer pain, myofascial pain (muscular injury, fibromyalgia) and perioperative pain (general surgery, gynecologic surgery).

The compounds of formulae (I) and (Ia) are particularly useful In the treatment or prevention of chronic pain, especially inflammatory, e.g., chronic inflammatory pain; inflammatory diseases, e.g., inflammatory airways disease, e.g., chronic obstructive pulmonary disease (COPD), or in asthma; cough; urinary incontinence; migraine; visceral disorders, e.g., inflammatory bowel disease; rhinitis; cystitis, e.g. interstitial cystitis; pancreatitis; uveitis; inflammatory skin disorders; and rheumatoid arthritis.

The compounds of formulae (I) and (Ia) are thus useful as vanilloid receptor antagonists, e.g., for the treatment of pain of various genesis or aetiology and as anti-inflammatory and/or anti-edemic agents for the treatment of inflammatory reactions, diseases or conditions, as well as for the treatment of allergic responses. Having regard to their analgesic/anti-inflammatory profile, they are useful for the treatment of inflammatory pain, for the treatment of hyperalgesia and, in particular, for the treatment of severe chronic pain. They are, e.g., useful for the treatment of pain, inflammation and/or oedema consequential to trauma, e.g., associated with burns, sprains, fractures or the like, subsequent to surgical intervention, e.g., as post-operative analgesics, as well as for the treatment of inflammatory pain of diverse genesis, e.g., for the treatment of osteo and rheumatoid arthritis and rheumatic disease, teno-synovitis and gout. They are further suitable as analgesics for the treatment of pain associated with, e.g., angina, menstruation or cancer. As anti-inflammatory/anti-oedema agents, they are further useful, e.g., for the treatment of inflammatory skin disorders, e.g., psoriasis and eczema.

As vanilloid receptor blockers, the compounds of formula (I) and (Ia) are also useful as smooth muscle relaxants, e.g., for the treatment of spasm of the gastrointestinal tract or uterus, e.g., in the therapy of Crohn's disease, ulcerative colitis or pancreatitis.

The compounds of formula (I) and (Ia) are in particular useful as agents for the therapy of airways hyperreactivity and for the treatment of inflammatory events associated with airways disease, in particular, asthma. In addition, the agents of invention may, e.g., be used for the control, restriction or reversal of airways hyperreactivity in asthma.

Inflammatory or obstructive airways diseases to which the present invention is applicable include asthma of whatever type or genesis including both intrinsic and, especially, extrinsic asthma. Thus, the compounds of formula (I) and (Ia) are useful for the treatment of allergic asthma, as well as, e.g., exercise induced asthma, occupational asthma, asthma induced following bacterial infection, other non-allergic asthmas and "wheezy-infant syndrome".

Efficacy in the treatment of asthma will be evidenced by reduced frequency or severity of symptomatic attack, e.g., of acute asthmatic or bronchoconstrictor attack and by reduced requirement for other, symptomatic therapy, e.g., anti-inflammatory, e.g., corticosteroid; or bronchodilator, e.g., β2 adrenergic, therapy.

Inflammatory or obstructive airways diseases to which the present invention is applicable further include pneumoconiosis (an inflammatory, commonly occupational, disease of the lungs, frequently accompanied by repeated inhalation of dusts) of whatever type or genesis including, e.g., aluminosis, anthracosis, asbestosis, chalicosis, ptilosis, siderosis, silicosis, tabacosis and, in particular, byssinosis.

Further inflammatory or obstructive airways diseases and conditions for which the compounds of formulae (I) and (Ia) may be used include adult respiratory distress syndrome (ARDS), chronic obstructive pulmonary or airways disease (COPD or COAD), and bronchitis. The compounds of formulae (I) and (Ia) may also be used for the treatment of allergic and vasomotor rhinitis.

In addition to the foregoing, the compounds of formulae (I) and (Ia) are also indicated for use in the therapy of septic shock, e.g., as anti-hypovolaemic and/or anti-hypotensive agents; in the treatment of inflammatory bowel disease; cerebral oedema; headache; migraine; inflammatory skin disease, such as eczema and psoriasis; inflammatory disorders of the gut, e.g., irritable bowel syndrome; Crohn's disease; ulcerative colitis; and cystitis, e.g., interstitial cystitis, nephritis and uveitis.

The agents of the invention are useful in the prevention and treatment of diseases and conditions in which human VR1 activation plays a role or is implicated, and therefore susceptible to treatment by the modulation (preferably antagonism) of VR1 receptors. Such conditions include chronic pain with an inflammatory component such as rheumatoid arthritis; bone and joint pain (osteoarthritis); post-surgical pain; musculo-skeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, abdominal pain, gynaecological pain, such as dysmenorrhoea, and labour pain; pain associated with the urogenital tract such as cystitis and vulvadynia; inflammatory skin disorders, for example psoriasis and eczema, or itch of non-specific origin; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; central nervous system pain, such as pain due to spinal cord or brain stem damage, or stroke; gout; scar pain; pain associated with carcinoma, often referred to as cancer pain; respiratory diseases including asthma, aluminosis, anthracosis, inflammatory airways disease, e.g. Chronic Obstructive Pulmonary Disease; chronic bronchitis, asbestosis, chalicosis, ptilosis, siderosis, silicosis, tabacosis, byssinosis; rhinitis including allergic rhinitis such as seasonal and perennial rhinitis, and non-allergic rhinitis; cough, either idiopathic or associated with respiratory diseases such as COPD, asthma, cystic fibrosis, cancer, or gastrointestinal disturbances such as gastro-oesophageal reflux; autoimmune diseases; gastrointestinal disorders including but not restricted to irritable bowel syndrome, Crohn's disease, ulcerative colitis, pancreatitis, inflammatory bowel disease. Diseases of the urogenital tract, particularly cystitis; urinary incontinence including bladder detrusor hyper-reflexia and bladder hypersensitivity.

For the above-mentioned indications, the appropriate dosage will of course vary depending upon, e.g., the compound employed, the host, the mode of administration and the nature and severity of the condition being treated. However, in general, satisfactory results in animals are indicated to be obtained at a daily dosage of from about 0.05 to about 150, preferably from about 0.1 mg/kg to about 100 mg/kg animal body weight. In larger mammals, e.g., humans, an indicated daily dosage is in the range from about 0.5 to about 5,000, preferably from about 1 mg to about 500 mg of a compound of formulae (I) and (Ia), conveniently administered, e.g., in divided doses up to four times a day or in sustained-release form.

The compounds of formulae (I) and (Ia) can be administered in vivo either alone or in combination with other pharmaceutical agents effective in the treatment of diseases and conditions in which vanilloid receptor activation plays a role or is implicated including cyclooxygenase-2 (COX-2) inhibitors, such as specific COX-2 inhibitors, e.g., celecoxib and rofecoxib; and non-steroidal anti-inflammatory drugs (NSAIDs), e.g., acetylsalicylic acid and propionic acid derivatives; tricyclic anti-depressants, e.g., Anafranil®, Asendin®, Aventyl®, Elavil®, Endep®, Norfranil®, Norpramin®, Pamelor®, Sinequan®, Surmontil®, Tipramine®, Tofranil®, Vivactil®, Tofranil-PM®; anti-convulsants, e.g., carbamazepine, oxcarbazepine and gabapentin; bradykinin B1 or B2 antagonists; and $GABA_B$ agonists, e.g., L-baclofen.

The agents of the invention can be administered in vivo either alone or in combination with other pharmaceutical agents, e.g. agents effective in the treatment of diseases and conditions in which the human VR1 activation plays a role or is implicated, such as cyclooxygenase inhibitors, including specific COX-2 inhibitors (e.g. celecoxib, lumiracoxib, and valdecoxib) or in general nonsteroidal anti-inflammatory drugs (NSAIDs) (e.g. acetylsalicylic acid, propionic acid derivatives), anti-migraine agents such as 5-HTi agonists and CGRP antagonists, tricyclic antidepressants (e.g. clomipramine, amoxapine, nortripyline, amitriptyline, imipramine, desipramine, doxepin, trimipramine, protripyline) selective serotonic reuptake inhibitors (e.g. fluoxetine), selective noradrenaline reuptake inhibitors (e.g. duloxetine), anticonvulsants (e.g. gabapentin, pregabalin, oxcarbazepine, carbamazepine), $GABA_B$ agonists (e.g. L-baclofen), opioids (e.g. morphine), $CB_1$ receptor agonists, bradykinin receptor antagonists, substance P antagonists.

The pharmaceutical compositions for separate administration of the combination partners and for the administration in a fixed combination, i.e., a single galenical composition comprising at least two combination partners, according to the invention can be prepared in a manner known per se and are those suitable for enteral, such as oral or rectal, and parenteral administration to mammals, including man, comprising a therapeutically effective amount of at least one pharmacologically active combination partner alone or in combination with one or more pharmaceutically acceptable carriers, especially suitable for enteral or parenteral application.

Pharmaceutical compositions contain, e.g., from about 0.1% to about 99.9%, preferably from about 20% to about 60%, of the active ingredients. Pharmaceutical preparations for the combination therapy for enteral or parenteral administration are, e.g., those in unit dosage forms, such as tablets including sugar-coated tablets, capsules, suppositories and ampoules. These are prepared in a manner known, per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

A further aspect of the instant invention involves the "novel" compositions comprising a pharmaceutically acceptable carrier or diluent and a therapeutically effective amount of a compound of formula (Ia), in free or salt form and, where possible, in acid addition salt form.

In accordance with the foregoing, the present invention also provides:

(1) A compound of formula (I) or (Ia) in free or salt form and, where possible, in pharmaceutically acceptable acid addition salt form for use as a vanilloid receptor blocker, e.g., for use in any of the particular indications set forth hereinabove;

(2) A compound of formula (I) or (Ia) in free or salt form and, where possible, in pharmaceutically acceptable acid addition salt form for the treatment of a disease or condition in which vanilloid receptor plays a role or is implicated;

(3) A method for the treatment of any of the particular indications set forth hereinabove in a subject in need thereof which comprises administering a therapeutically effective amount of a compound of formula (I) or (Ia) in free or salt form and, where possible, in pharmaceutically acceptable acid addition salt form;

(4) A method for treating or preventing a disease or condition in which vanilloid receptor plays a role or is implicated comprising administering to a mammal in need thereof a therapeutically effective amount of a compound of formula (I) or (Ia) in free or salt form and, where possible, in pharmaceutically acceptable acid addition salt form;

(5) Use of a compound of formula (I) or (Ia) in free or salt form and, where possible, in pharmaceutically acceptable acid addition salt form for the manufacture of a medicament for the treatment or prevention of a disease or condition in which activity of vanilloid receptor plays a role or is implicated;

(6) A method as set forth hereinabove comprising co-administration, e.g., concomitantly or in sequence, of a therapeutically effective amount of a vanilloid receptor antagonist, e.g., a compound of formula (I) or (Ia) in free or salt form and, where possible, in pharmaceutically acceptable acid addition salt form and a second drug substance, said second drug substance being, e.g., for use in any of the particular indications set forth hereinabove; and (7) A combination comprising a therapeutically effective amount of a compound of formula (I) or (Ia) in free or salt form and, where possible, in pharmaceutically acceptable acid addition salt form and a second drug substance, said second drug substance being, e.g., for use in any of the particular indications set forth hereinabove.

In the Examples which follow, which are not intended to limit, in any way, the scope of the present invention, the following abbreviations are used:
EtOAc ethyl acetate
DCM dichloromethane

Example 1

Preparation of 7-amino-3-(4-chlorophenyl)-2-isopropyl-3H-quinazolin-4-one a) Preparation of 3-(4-chlorophenyl)-2-isopropyl-7-nitro-3H-quinazolin-4-one A suspension of 4-nitroanthranilic acid isobutyramide (4 g, 15.8 mmol), 4-chloroaniline (2.2 g, 17.2 mmol) and phosphorus trichloride (5.6 mL) in toluene (150 mL) is heated to reflux (bath temperature for 150° C.) for 2 hours. The reaction mixture is allowed to cool to room temperature and then evaporated to dryness. The residue is partitioned between water and EtOAc and the aqueous phase is extracted (2×) with EtOAc. The combined organic phases are washed with water, dried ($Na_2SO_4$) and evaporated in vacuo. Trituration with isopropyl ether provides the desired compound as a brown solid.

b) Preparation of the Title Compound

A mixture of the compound prepared in Example 1a above (2.4 g, 6.98 mmol), iron powder (1.16 g, 20.8 mmol) and glacial acetic acid (70 mL) is stirred at 50° C. for 2.5 hours. The reaction mixture is allowed to cool to room temperature and then evaporated in vacuo to dryness. The residue is partitioned between water and EtOAc and the aqueous phase is extracted (2×) with EtOAc. The combined organic phases are washed with water, dried ($Na_2SO_4$) and evaporated in vacuo to give a brown solid. Purification by automated flash chromatography (gradient elution: EtOAc/DCM 0-50%) provides the title compound as a pale yellow solid.

$(M+H)^+=314.2$; HPLC retention time=3.9 minutes.

Example 2

Preparation of 3-(4-chlorophenyl)-7-hydroxy-2-isopropyl-3H-quinazolin-4-one

To a suspension of the compound of Example 1 (778 mg, 2.479 mmol) in concentrated sulphuric acid/water 972 µL/1.4 mL, cooled to ice bath temperature, is added a solution of sodium nitrite (188 mg) in water (680 µL). The mixture is stirred for 45 minutes at 0-5° C. (internal temperature) and then added to sulphuric acid/water 3/2 (5 mL), pre-heated to 150° C. After stirring for 15 minutes, the mixture is allowed to cool to room temperature, filtered and extracted with EtOAc (3×). The combined EtOAc extracts are washed with water, dried ($Na_2SO_4$) and evaporated to a yellow-orange solid. Purification by automated flash chromatography (gradient elution: EtOAc/hexane 0-25%) provides the title compound as a yellow solid.

$^1$H NMR (400 MHz, MeOH-$d_4$): δ 7.91 (1H, d, J=8.7 Hz), 7.49 (2H, d, J=9.5 Hz), 7.25 (2H, d, J=9.5 Hz), 6.93 (1H, d, J=2.3 Hz), 6.86 (1H, dd, J=2.3, 8.7 Hz), 2.56 (1H, quint, J=6.7 Hz), 1.11 (6H, d, J=6.7 Hz); $(M+H)^+=315.8$; HPLC retention time=4.2 minutes.

Examples 3 to 28

The compounds of Examples 3 to 28 can be prepared in a manner analogous to that described in the previous Examples.

| Example | Structure | $(M + H)^+$ | HPLC Retention Time (in minutes) | Method of Preparation |
|---|---|---|---|---|
| 3 | 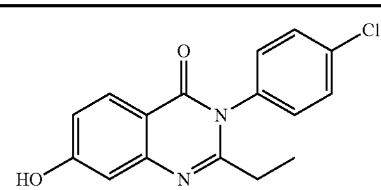 | 302.0 | 3.5 | Schemes A + B |
| 4 | 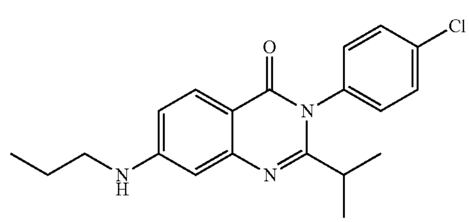 | 356.3 | 5.6 | Scheme A + Reductive Alkylation |
| 5 | 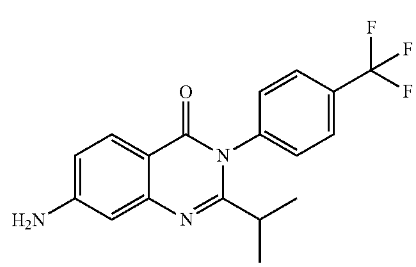 | 348.2 | 4.3 | Scheme A |

-continued
| Example | Structure | (M + H)+ | HPLC Retention Time (in minutes) | Method of Preparation |
|---|---|---|---|---|
| 6 | 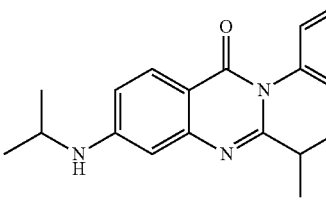 | 356.3 | 5.5 | Scheme A + Reductive Alkylation |
| 7 | 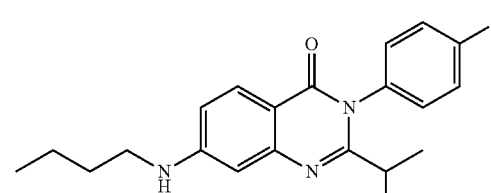 | 370.3 | 6.2 | Scheme A + Reductive Alkylation |
| 8 | 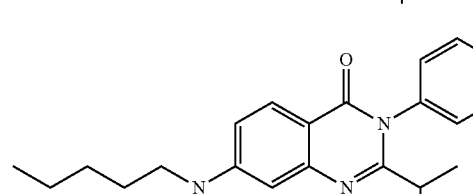 | 384.3 | 6.7 | Scheme A + Reductive Alkylation |
| 9 | 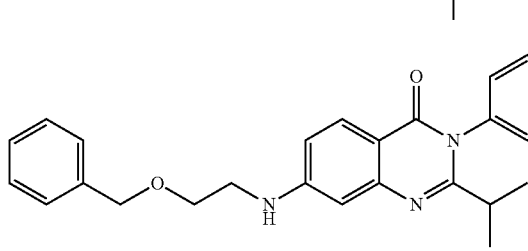 | 448.3 | 6.2 | Scheme A + Reductive Alkylation |
| 10 | 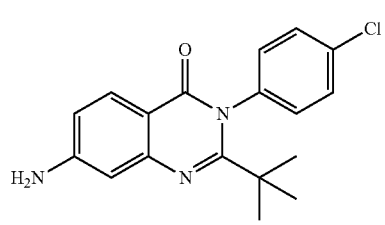 | 328.2 | 4.9 | Scheme A |
| 11 | 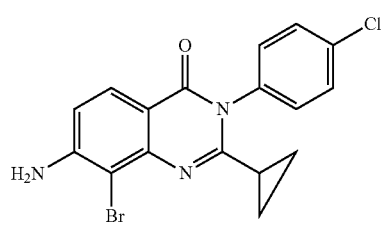 | 391.7 | 5.4 | Scheme A + Selective Halogenation |
| 12 | 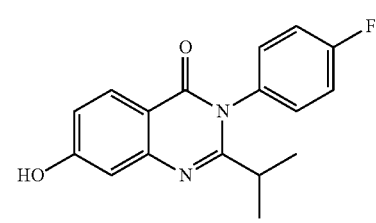 | 300.0 | 3.6 | Schemes A + B |

-continued

| Example | Structure | (M + H)+ | HPLC Retention Time (in minutes) | Method of Preparation |
|---|---|---|---|---|
| 13 | 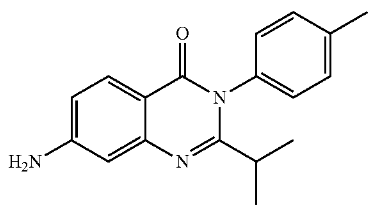 | 295.0 | 3.4 | Scheme A |
| 14 | 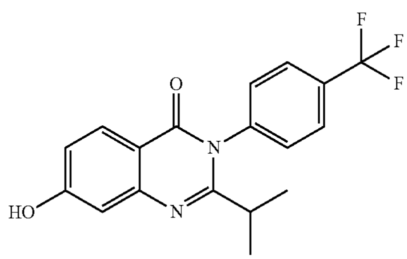 | 349.0 | 4.6 | Schemes A + B |
| 15 | 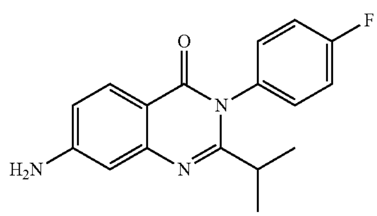 | 298.3 | 3.2 | Scheme A |
| 16 | 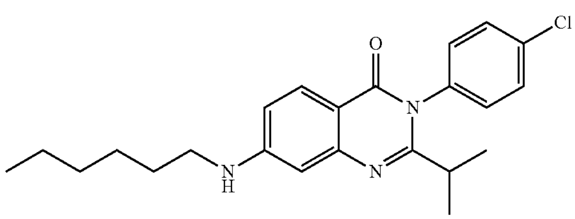 | 398.4 | 7.2 | Scheme A + Reductive Alkylation |
| 17 | 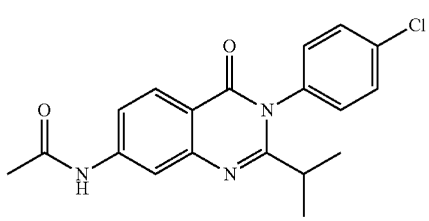 | 384.3 | 5.1 | Scheme A + N-Acylation |
| 18 | 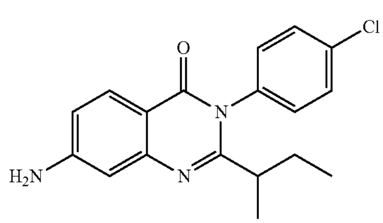 | 329.0 | 5.9 | Scheme A |

-continued

| Example | Structure | (M + H)+ | HPLC Retention Time (in minutes) | Method of Preparation |
|---|---|---|---|---|
| 19 | 7-amino-3-(4-fluorophenyl)-2-cyclopropyl quinazolin-4(3H)-one | 297.0 | 3.1 | Scheme A |
| 20 | 3-(4-chlorophenyl)-2-cyclopropyl-7-hydroxyquinazolin-4(3H)-one | 313.9 | 4.1 | Schemes A + B |
| 21 | 2-(sec-butyl)-3-(4-chlorophenyl)-7-hydroxyquinazolin-4(3H)-one | 329.0 | 4.6 | Schemes A + B |
| 22 | 8-chloro-3-(4-chlorophenyl)-7-hydroxy-2-isopropylquinazolin-4(3H)-one | 350.2 | 5.3 | Schemes A + B + Selective Halogenation |
| 23 | 7-amino-3-(4-chlorophenyl)-2-cyclopentylquinazolin-4(3H)-one | 341.0 | 4.7 | Scheme A |
| 24 | 3-(4-chlorophenyl)-2-cyclopentyl-7-hydroxyquinazolin-4(3H)-one | 341.0 | 4.6 | Schemes A + B |

-continued

| Example | Structure | (M + H)⁺ | HPLC Retention Time (in minutes) | Method of Preparation |
|---|---|---|---|---|
| 25 | *4-F-phenyl on N3; 2-cyclopropyl; 7-HO quinazolin-4(3H)-one* | 298.0 | 3.5 | Schemes A + B |
| 26 | *4-Cl-phenyl on N3; 2-isopropyl; 7-H₂N, 8-Cl quinazolin-4(3H)-one* | 349.2 | 5.5 | Schemes A + Selective Halogenation |
| 27 | *4-Cl-phenyl on N3; 2-isopropyl; 7-HO, 8-Br quinazolin-4(3H)-one* | 394.7 | 5.5 | Schemes A + B + Selective Halogenation |
| 28 | *4-Cl-phenyl on N3; 2-isopropyl; 7-H₂N, 8-Br quinazolin-4(3H)-one* | 393.7 | 5.7 | Scheme A + Selective Halogenation |

Example 29

The compounds 29.1 to 29.54 can be prepared in a manner analogous to that described in the previous Examples.

| No. | Structure | HPLC Retention Time (in minutes) | (M + H)⁺ |
|---|---|---|---|
| 29.1 | *4-Cl-phenyl on N3; 2-isopropyl; 7-HO, 8-O-CH₂-cyclopropyl quinazolin-4(3H)-one* | 5.7 | 385.3 |

-continued

| No. | Structure | HPLC Retention Time (in minutes) | (M + H)+ |
| --- | --- | --- | --- |
| 29.2 | 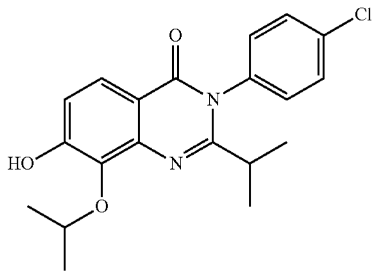 | 8.0 | 373.4 |
| 29.3 | 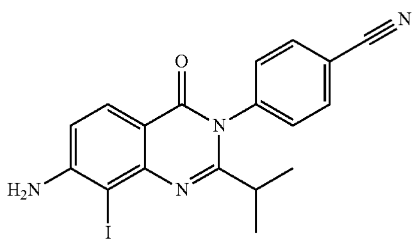 | 5.2 | 431.1 |
| 29.4 | 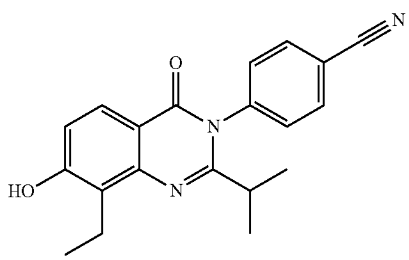 | 7.6 | 334.3 |
| 29.5 | 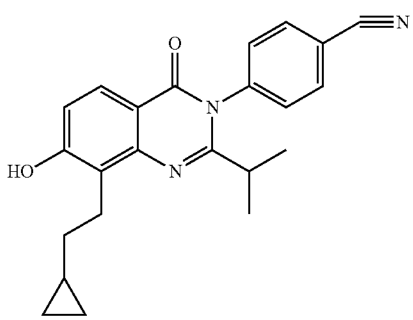 | 4.8 | 376.0 |
| 29.6 | 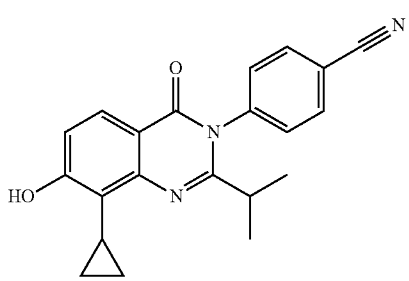 | 5.1 | 346.2 |

-continued

| No. | Structure | HPLC Retention Time (in minutes) | (M + H)+ |
|---|---|---|---|
| 29.7 | 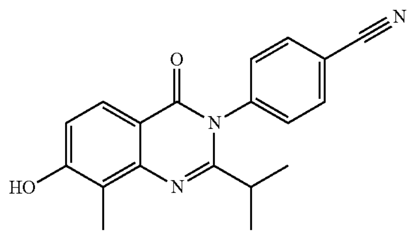 | 4.7 | 320.2 |
| 29.8 | 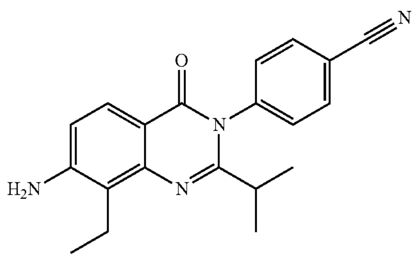 | 5.1 | 333.2 |
| 29.9 | 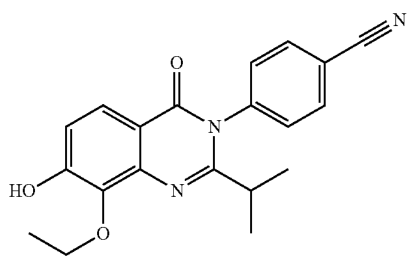 | 4.3 | 350.3 |
| 29.10 | 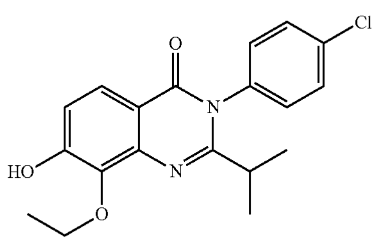 | 5.2 | 359.3 |
| 29.11 | 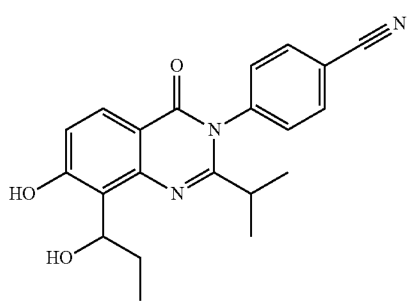 | 4.5 | 364.4 |
| 29.12 | 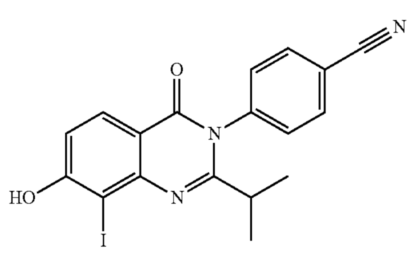 | 5.0 | 432.2 |

-continued

| No. | Structure | HPLC Retention Time (in minutes) | (M + H)+ |
| --- | --- | --- | --- |
| 29.13 | 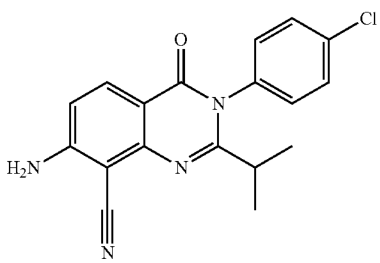 | | 340.2 |
| 29.14 | 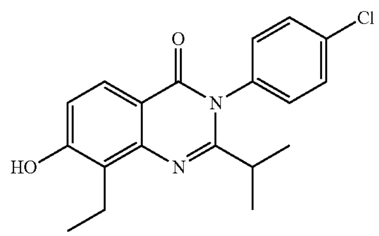 | 6.1 | 343.0 |
| 29.15 | 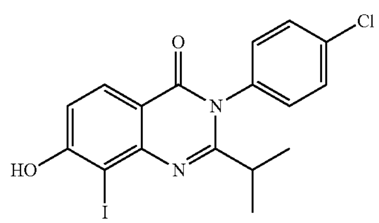 | 5.8 | 441.2 |
| 29.16 | 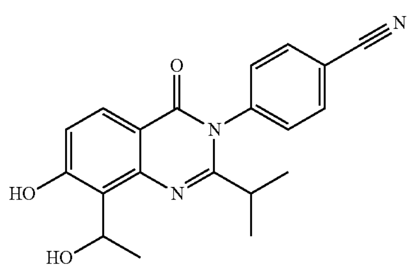 | 4.0 | 350.3 |
| 29.17 | 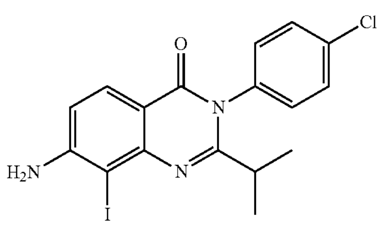 | 6.0 | 441.0 |
| 29.18 | 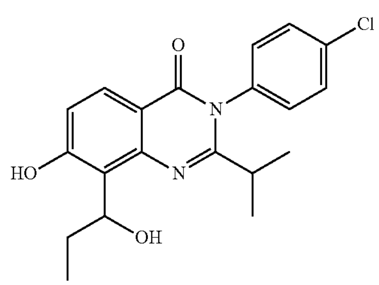 | 5.2 | 373.4 |

-continued

| No. | Structure | HPLC Retention Time (in minutes) | (M + H)+ |
|---|---|---|---|
| 29.19 | 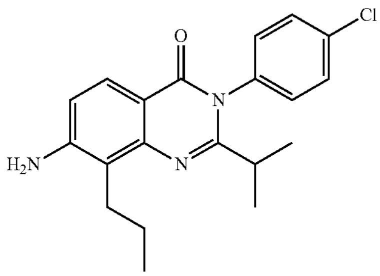 | 6.4 | 356.3 |
| 29.20 | 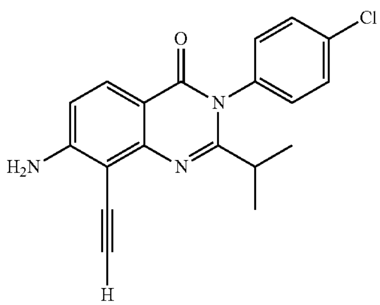 | 5.0 | 339.2 |
| 29.21 | 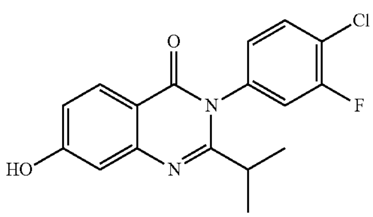 | 4.4 | 333.1 |
| 29.22 | 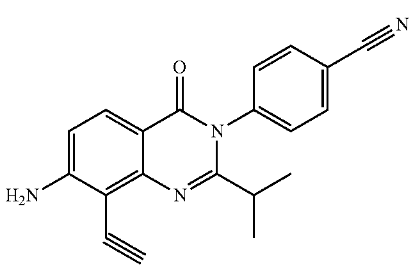 | 4.3 | 329.2 |
| 29.23 | 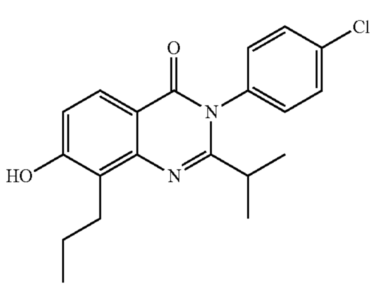 | 6.5 | 357.9 |

-continued
| No. | Structure | HPLC Retention Time (in minutes) | (M + H)+ |
|---|---|---|---|
| 29.24 | 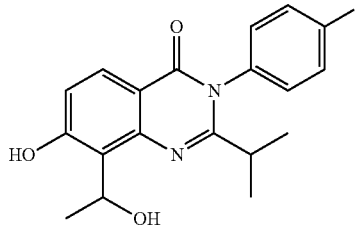 | 4.8 | 359.3 |
| 29.25 | 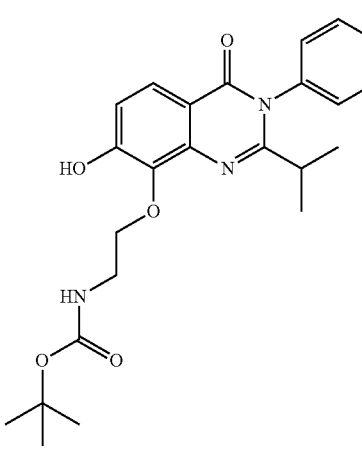 | 5.8 | 474.4 |
| 29.26 | 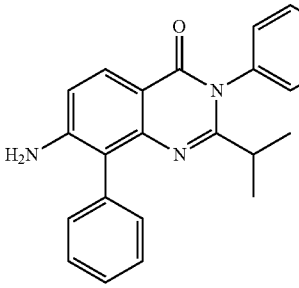 | 6.3 | 390.3 |
| 29.27 | 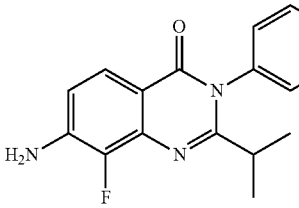 | 4.7 | 333.0 |
| 29.28 | 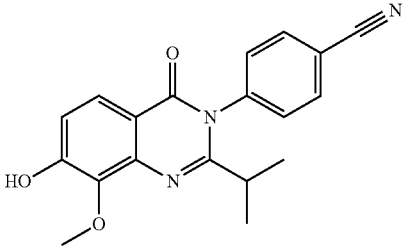 | 3.8 | 336.3 |

-continued

| No. | Structure | HPLC Retention Time (in minutes) | (M + H)+ |
|---|---|---|---|
| 29.29 | 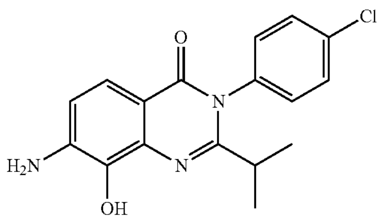 | 4.5 | 331.0 |
| 29.30 | 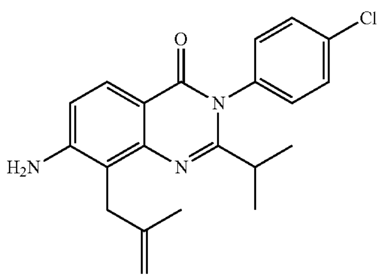 | 6.5 | 368.3 |
| 29.31 | 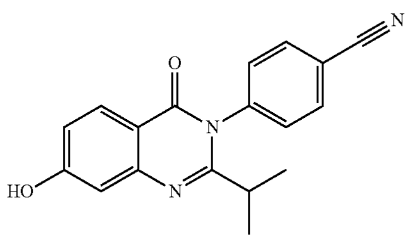 | 3.4 | 306.4 |
| 29.32 | 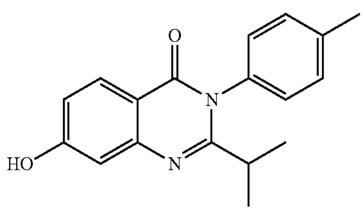 | 3.9 | 295.3 |
| 29.33 | 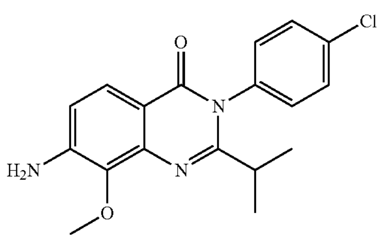 | 4.8 | 345.0 |
| 29.34 | 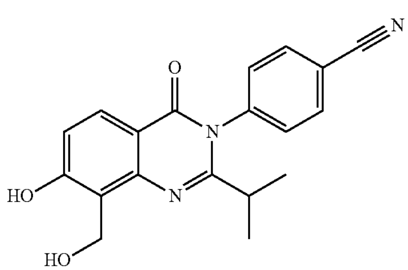 | 3.5 | 336.3 |

| No. | Structure | HPLC Retention Time (in minutes) | (M + H)+ |
|---|---|---|---|
| 29.35 | 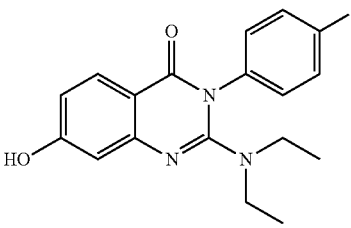 |  | 345.2 |
| 29.36 | 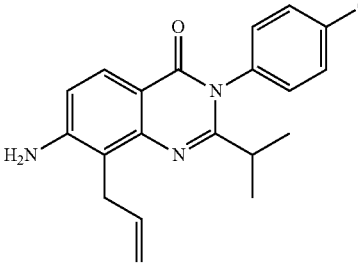 | 6.1 | 354.2 |
| 29.37 | 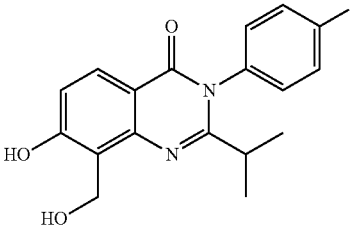 | 7.2 | 345.2 |
| 29.38 | 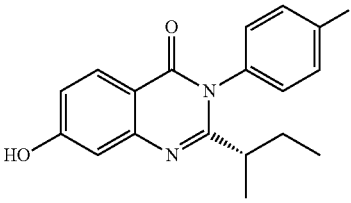 | 4.7 | 329.0 |
| 29.39 | 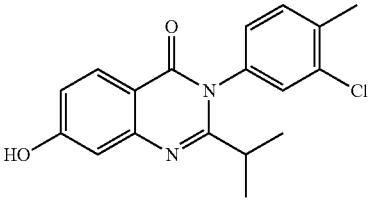 | 4.7 | 329.2 |
| 29.40 | 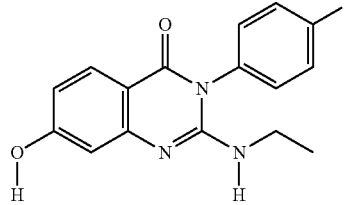 |  | 316.8 |

-continued

| No. | Structure | HPLC Retention Time (in minutes) | (M + H)+ |
|---|---|---|---|
| 29.41 | 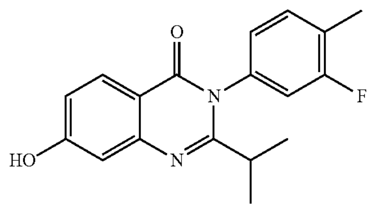 | 6.9 | 313.3 |
| 29.42 | 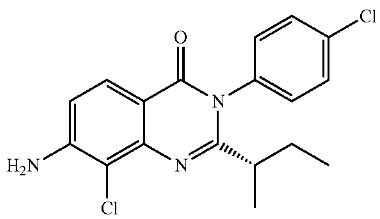 | 5.9 | 363.1 |
| 29.43 | 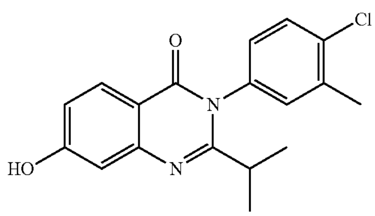 | 4.7 | 329.2 |
| 29.44 | 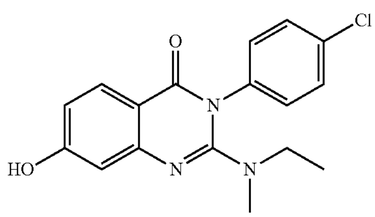 | | 331.2 |
| 29.45, | 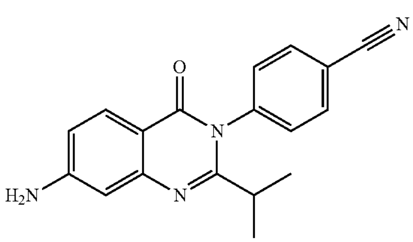 | 3.1 | 305.3 |
| 29.46 | 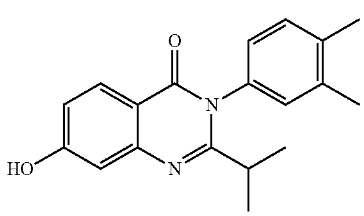 | 3.9 | 309.3 |

-continued
| No. | Structure | HPLC Retention Time (in minutes) | (M + H)+ |
|---|---|---|---|
| 29.47 | 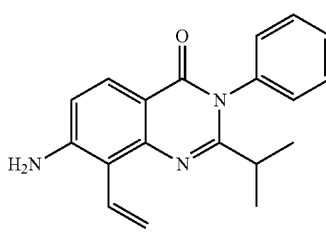 | 6.0 | 341.2 |
| 29.48 | 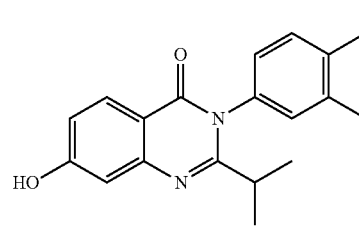 | 3.8 | 320.2 |
| 29.49 | 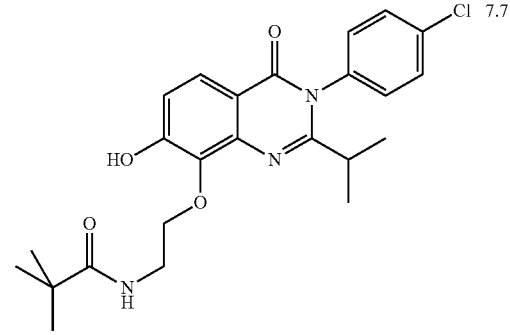 | 7.7 | 458.5 |
| 29.50 | 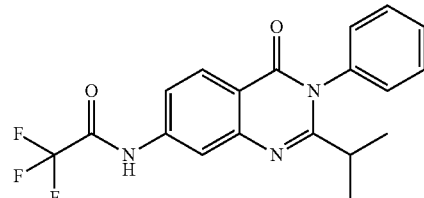 | 5.7 | 410.2 |
| 29.51 | 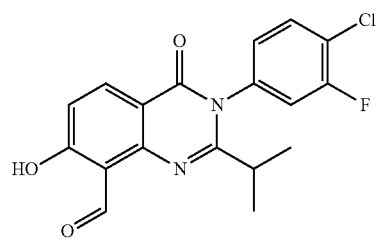 | 6.2 | 361.3 |
| 29.52 | 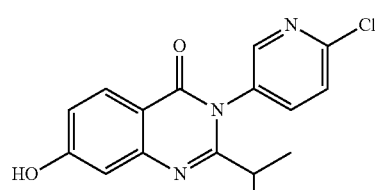 | 3.3 | 316.3 |

| No. | Structure | HPLC Retention Time (in minutes) | (M + H)+ |
|---|---|---|---|
| 29.53 | 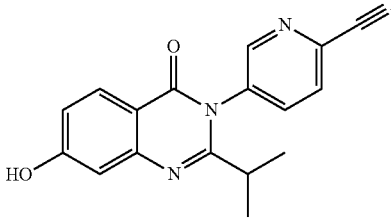 | 3.1 | 307.3 |
| 29.54 | 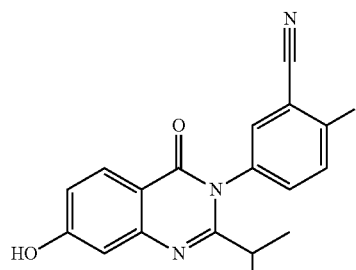 | 3.7 | 324.3 |

Example 30

Preparation of Soft Gelatin Capsules 5,000 soft gelatin capsules, each comprising as active ingredient 0.05 g of one of the compounds of formula (Ia) mentioned in the preceding Examples, are prepared as follows:
Composition
Active Ingredient 250 g
Lauroglykol® 2 l The pulverized active ingredient is suspended in Lauroglykol® (propylene glycol laurate, Gattefossé S. A., Saint Priest, France) and ground in a wet pulverizer to produce a particle size of about 1-3 μm. 0.419 g portions of the mixture are then introduced into soft gelatin capsules using a capsule-filling machine.

The invention claimed is:

1. A quinazolinone compound of the formula

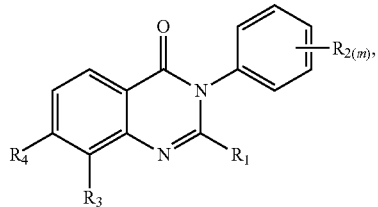

wherein
R$_1$ is C$_1$-C$_6$alkyl, (C$_1$-C$_6$alkyl)C$_1$-C$_6$alkyl, di-(C$_1$-C$_6$alkyl)C$_1$-C$_6$alkyl, or C$_3$-C$_6$cycloalkyl;
each R$_2$, independently, is cyano or a group —C(=O)—R$_{2a}$, where R$_{2a}$ is C$_1$-C$_6$alkyl;
R$_3$ is hydrogen, halogen, C$_1$-C$_6$alkyl, C$_2$-C$_6$alkenyl, C$_2$-C$_6$alkynyl, hydroxy, hydroxy-substituted C$_1$-C$_6$alkyl, C$_1$-C$_6$alkoxy, C$_3$-C$_6$cycloalkyl, cyano, —C(=O)H, phenyl, (C$_3$-C$_6$cycloalkyl)C$_1$-C$_6$alkoxy, (C$_1$-C$_6$alkoxycarbonylamino)C$_1$-C$_6$alkoxy or (C$_1$-C$_6$alkylcarbonylamino)C$_1$-C$_6$alkoxy;
R$_4$ is hydroxy, etherified hydroxy, a group —NHC(=O)R$_{4a}$ or a group —NHC(=O)OR$_{4a}$, where R$_{4a}$ is halogen-substituted C$_1$-C$_6$alkyl, or a group —NH(CH$_2$)$_2$OR$_{4b}$, where R$_{4b}$ is benzyl or phenylethyl; and
m is 1 or 2;
in free base form or in pharmaceutically acceptable salt form.

2. A compound according to claim 1 selected from

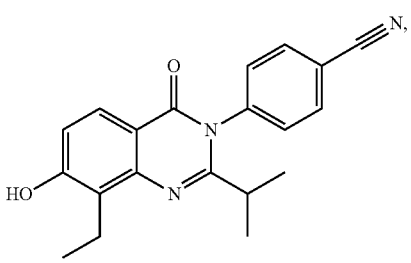

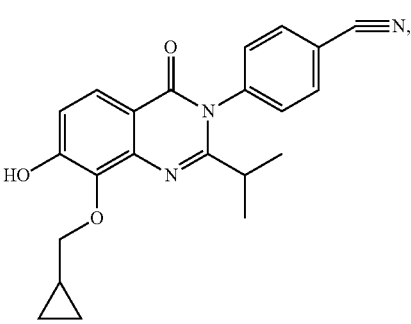

-continued

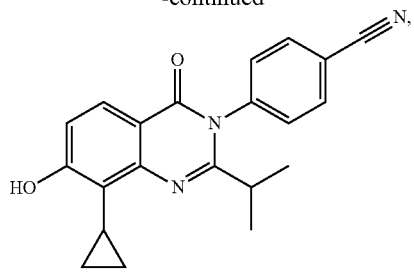

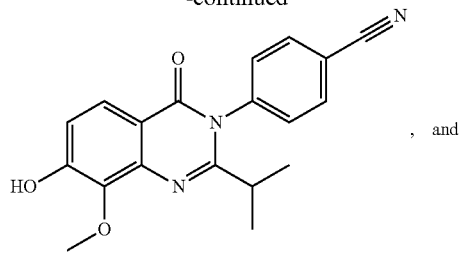

, and

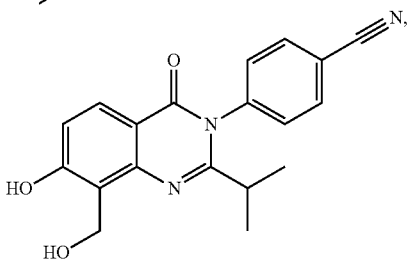

in free base form or in pharmaceutically acceptable salt form.

3. A compound according to claim 1 having the following formula

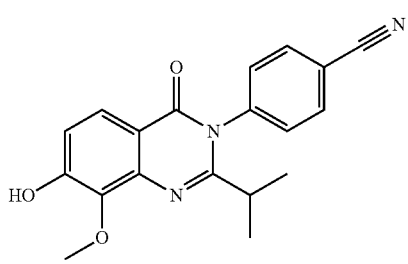

in free base form or in pharmaceutically acceptable salt form.

4. A compound according to claim 1 having the following formula

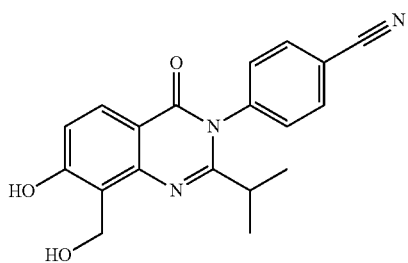

in free base form or in pharmaceutically acceptable salt form.

5. A compound according to claim 1 in free base form.
6. A compound according to claim 1 in pharmaceutically acceptable salt form.
7. A pharmaceutical composition comprising a compound according to claim 1, in free base form or in pharmaceutically acceptable salt form, as active ingredient and a pharmaceutically acceptable carrier or diluent.

* * * * *